(12) United States Patent
Tilson et al.

(10) Patent No.: US 10,966,763 B2
(45) Date of Patent: Apr. 6, 2021

(54) INFLATABLE MEDICAL DEVICES

(71) Applicant: LOMA VISTA MEDICAL, INC., Tempe, AZ (US)

(72) Inventors: Alexander Q. Tilson, Burlingame, CA (US); Mark C. Scheeff, San Francisco, CA (US)

(73) Assignee: LOMA VISTA MEDICAL, , INC., Tempe, AZ (US)

( * ) Notice: Subject to any disclaimer, the term of this patent is extended or adjusted under 35 U.S.C. 154(b) by 0 days.

(21) Appl. No.: 16/241,220

(22) Filed: Jan. 7, 2019

(65) Prior Publication Data
US 2019/0133649 A1     May 9, 2019

Related U.S. Application Data

(62) Division of application No. 13/293,058, filed on Nov. 9, 2011, now Pat. No. 10,188,436.

(60) Provisional application No. 61/411,778, filed on Nov. 9, 2010.

(51) Int. Cl.
| | |
|---|---|
| *A61B 17/88* | (2006.01) |
| *A61F 2/46* | (2006.01) |
| *A61C 5/62* | (2017.01) |
| *A61B 17/70* | (2006.01) |

(52) U.S. Cl.
CPC ...... *A61B 17/7097* (2013.01); *A61B 17/8816* (2013.01); *A61B 17/8822* (2013.01); *A61B 17/8805* (2013.01); *A61B 17/8808* (2013.01); *A61B 17/8811* (2013.01); *A61C 5/62* (2017.02); *A61F 2/4601* (2013.01)

(58) Field of Classification Search
CPC ............ A61B 17/8816; A61B 17/8822; A61B 17/8805; A61B 17/8808; A61B 17/8811; A61B 17/7095; A61C 5/62; A61C 17/0202; A61C 17/028; A61C 19/063; A61C 9/0026; A61F 2/4601; A61F 2/30723; B05C 17/00516; B05C 17/00593
USPC ........ 606/92–95; 604/11–18, 57–60; 433/87, 433/89, 90
See application file for complete search history.

(56) References Cited

U.S. PATENT DOCUMENTS

| | | | | |
|---|---|---|---|---|
| 833,044 | A * | 10/1906 | Goodhugh | A61C 5/62 433/90 |
| 1,469,004 | A * | 9/1923 | Holtz | B05C 17/00593 433/90 |
| 3,724,076 | A * | 4/1973 | Schmitz | B05C 17/00593 433/90 |
| 4,431,414 | A * | 2/1984 | Lawrence | B05C 17/00593 433/90 |
| 6,241,734 | B1 * | 6/2001 | Scribner | A61B 17/8816 606/93 |

(Continued)

*Primary Examiner* — Marcela I. Shirsat
(74) *Attorney, Agent, or Firm* — King & Schickli, PLLC

(57) ABSTRACT

A device for delivering a material to an orthopedic target site is disclosed. The device can be used to deliver bone cement to an intra-vertebral site. The device can have a pusher rod within a tube. The tube can be loaded with the bone cement distal to the pusher rod. The pusher rod can have varying rigidity along the length of the pusher rod. The tube and pusher rod can navigate tortuous pathways from a percutaneous or transcutaneous insertion en route to the target site or to improve extracorporeal ergonomics. Methods for using the same are also disclosed.

12 Claims, 11 Drawing Sheets

(56) References Cited

U.S. PATENT DOCUMENTS

| | | | |
|---|---|---|---|
| 7,507,243 B2 * | 3/2009 | Lambrecht | A61B 5/1076 606/92 |
| D703,515 S * | 4/2014 | Martin | D8/343 |
| 2007/0162042 A1 * | 7/2007 | Dunker | A61B 17/8816 606/94 |
| 2008/0125784 A1 * | 5/2008 | Rabiner | A61B 17/7097 606/92 |

* cited by examiner

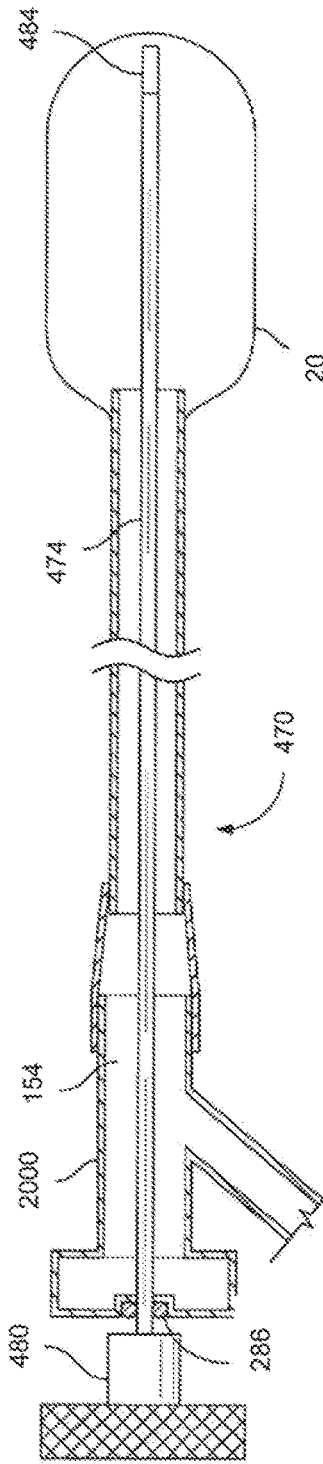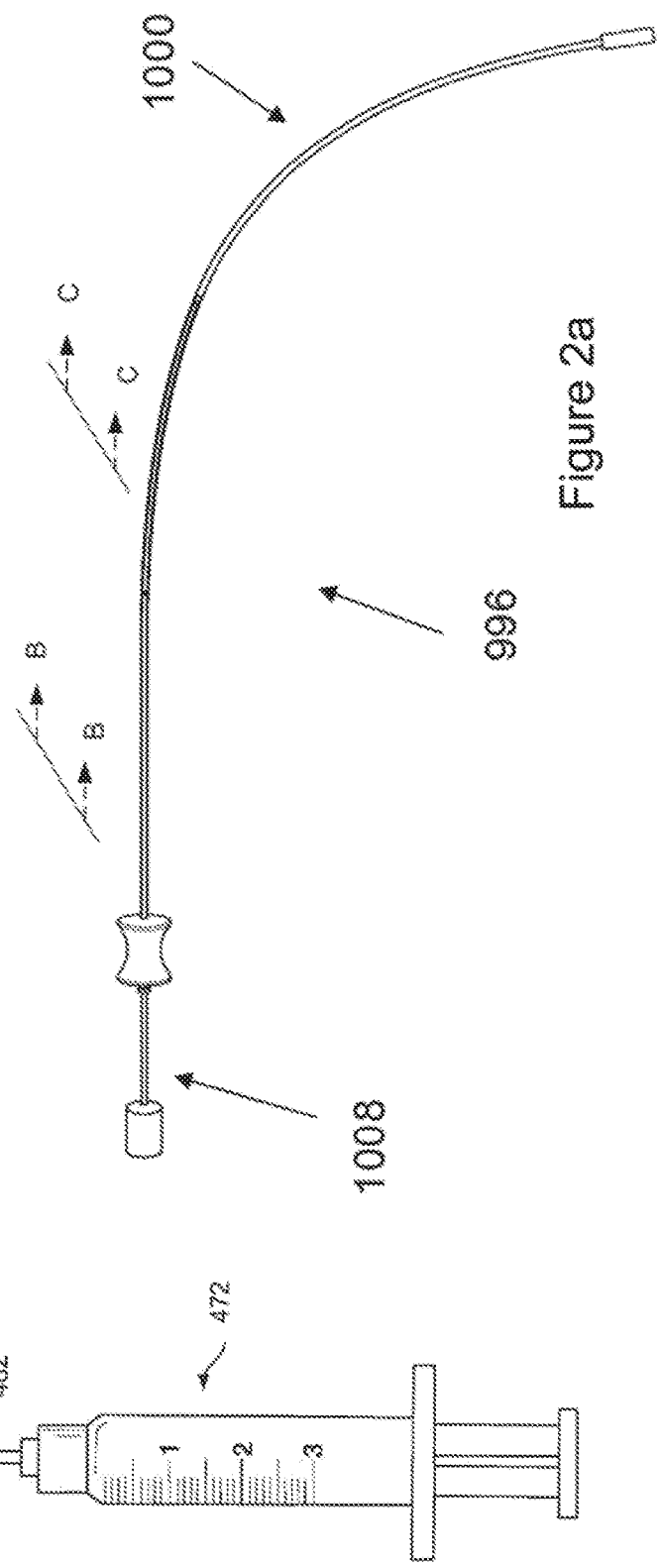

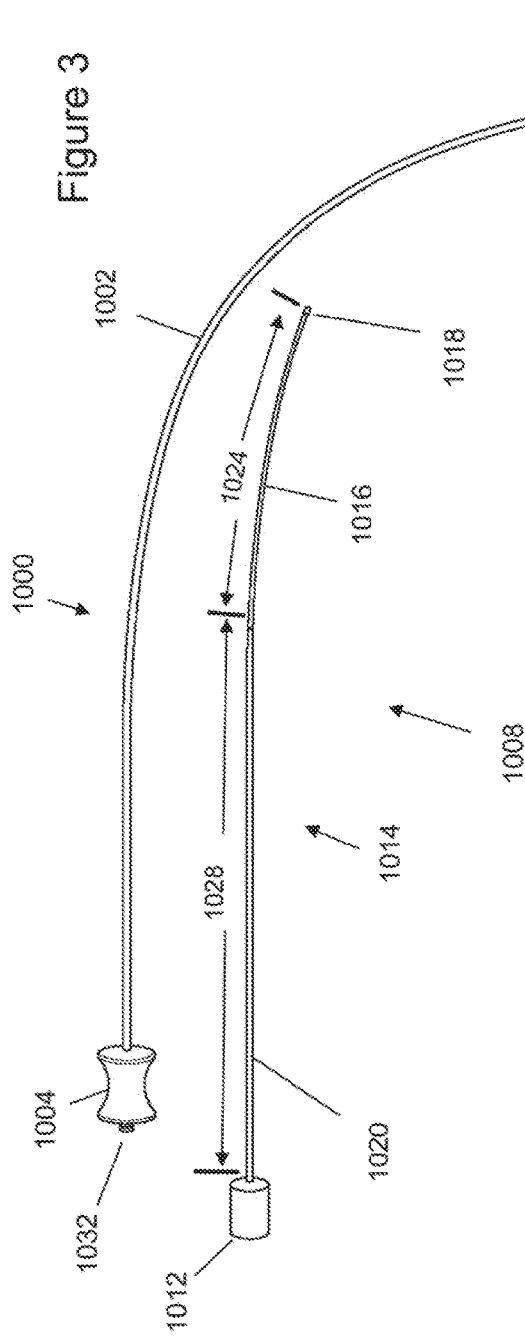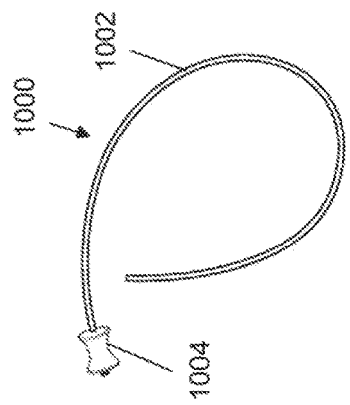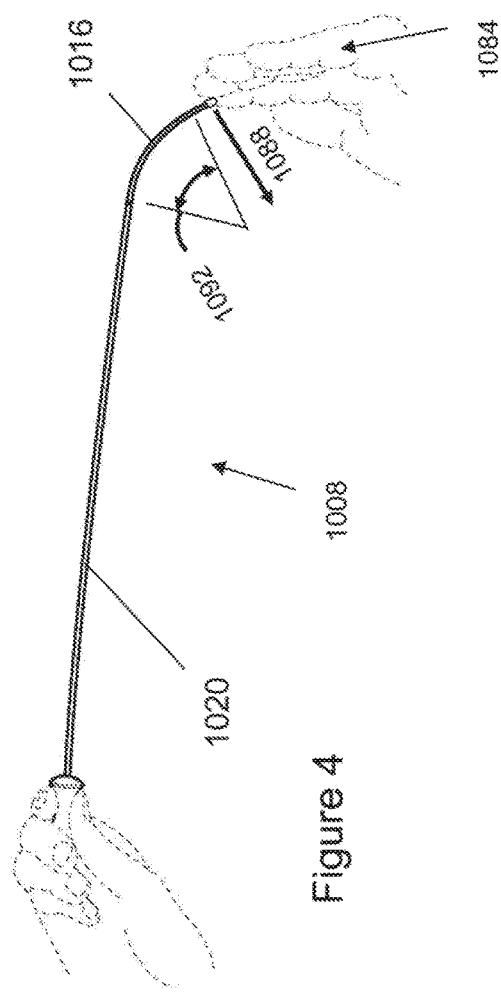

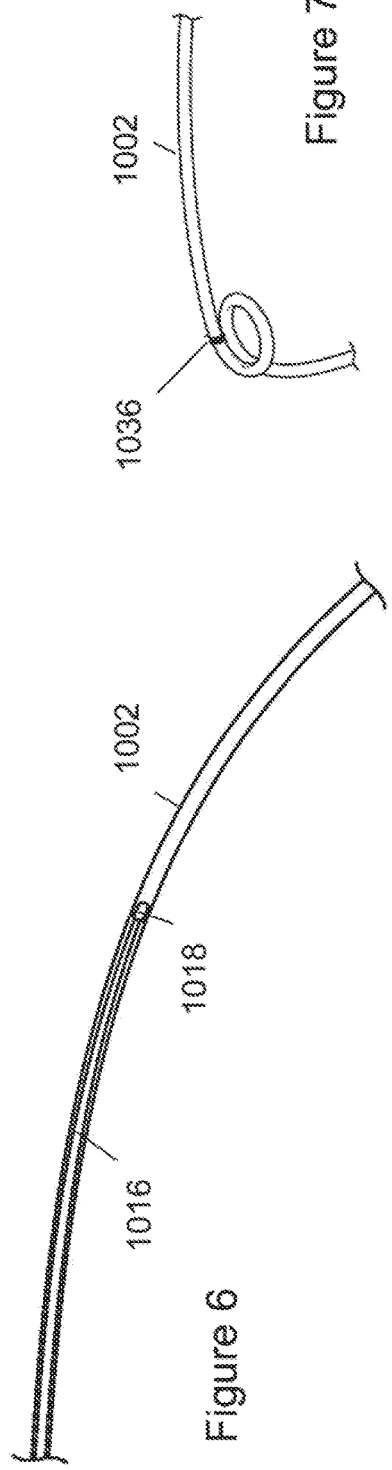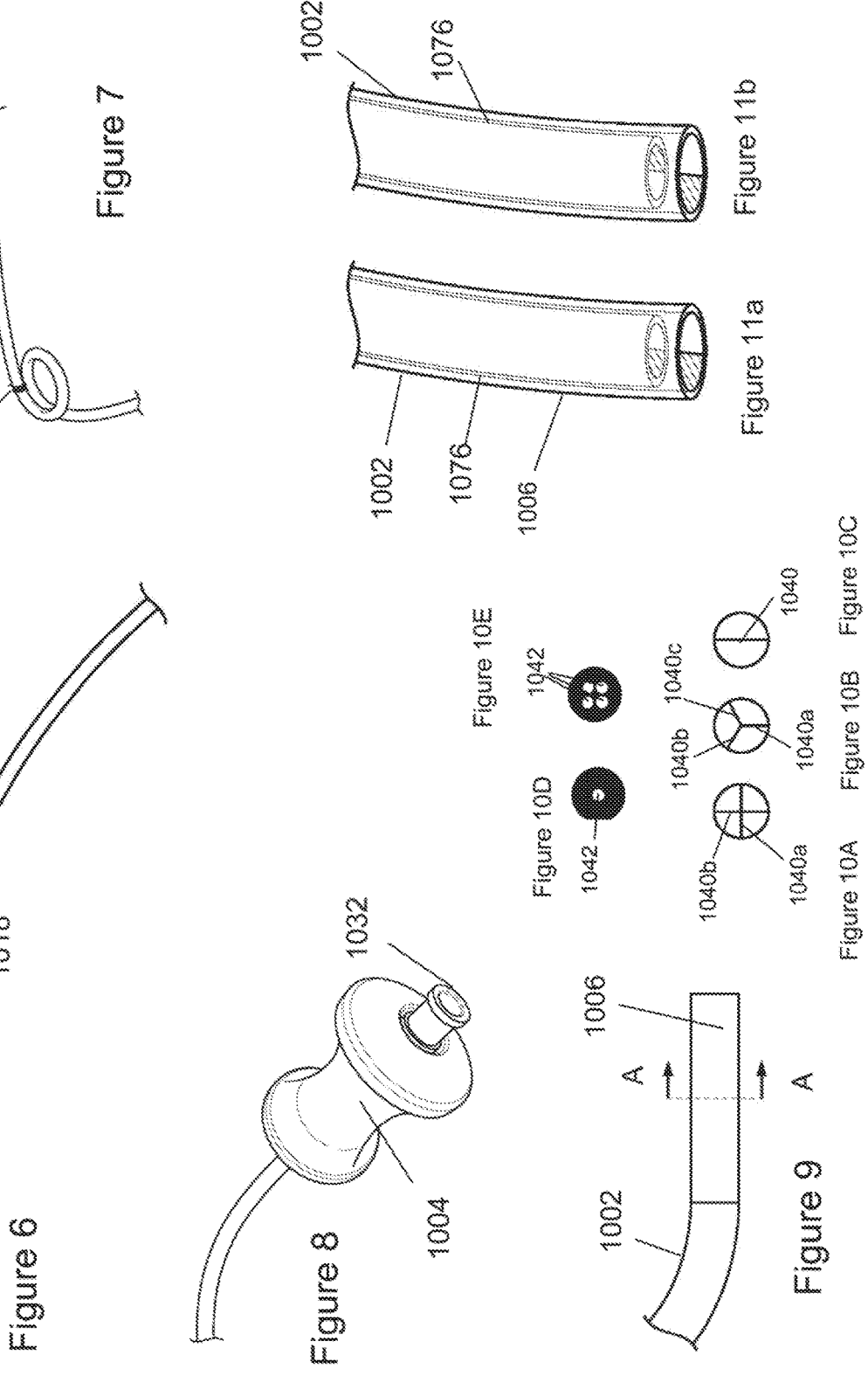

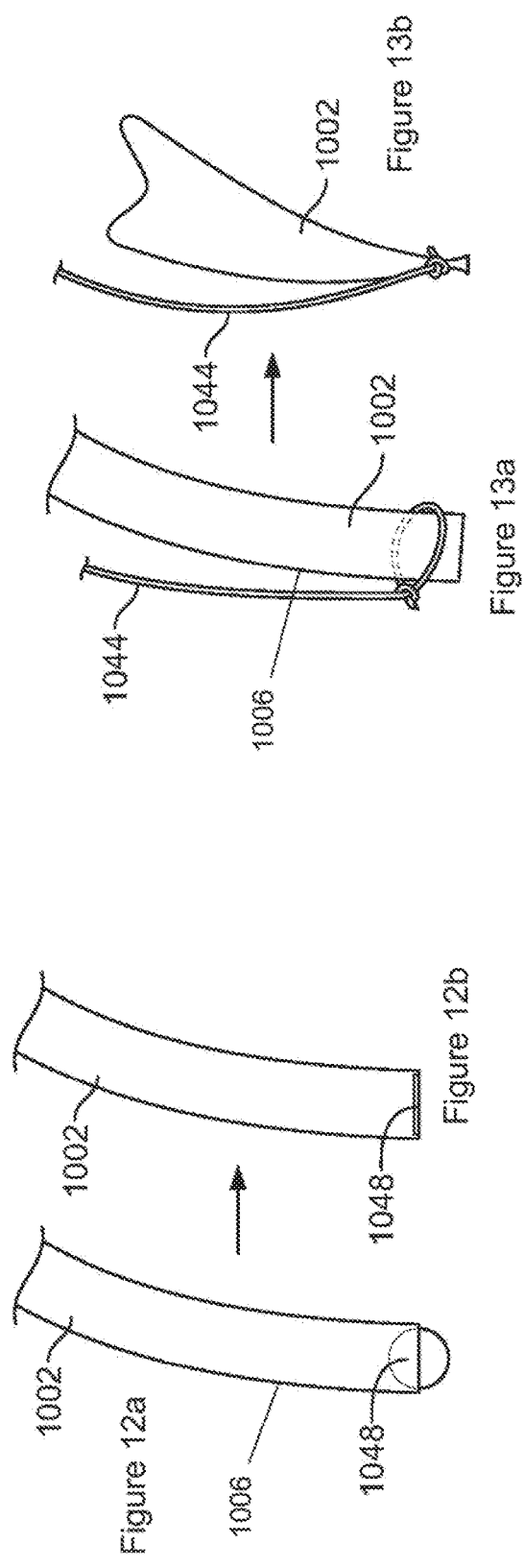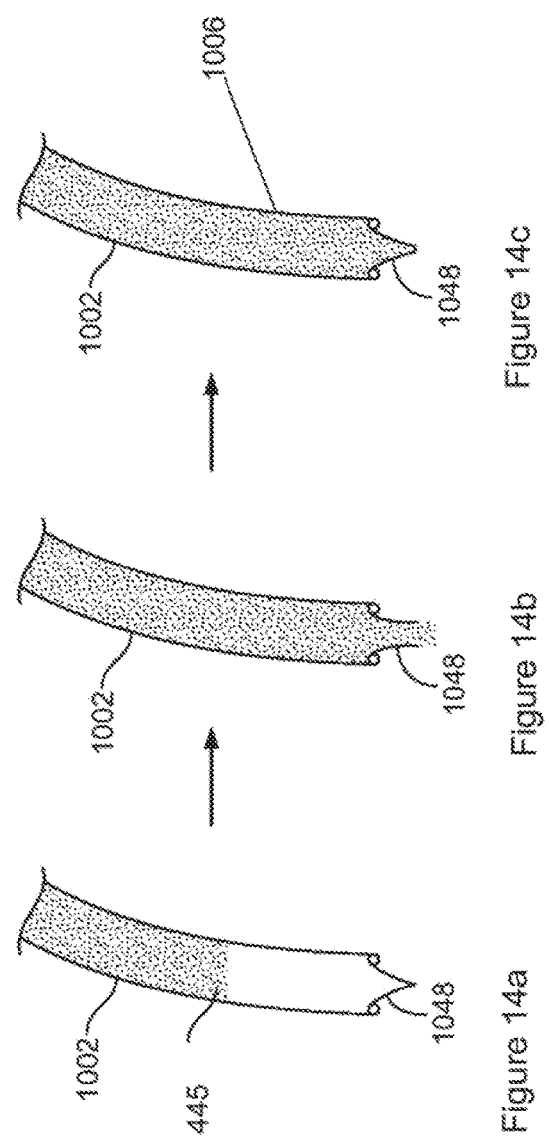

NOT INVENTION

NOT INVENTION

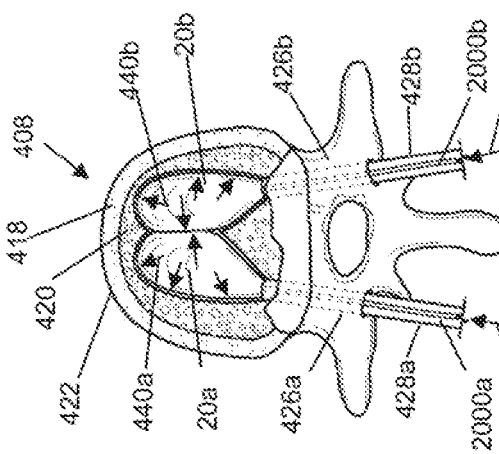
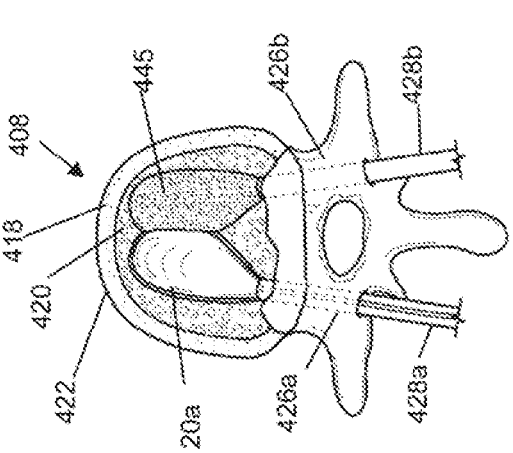
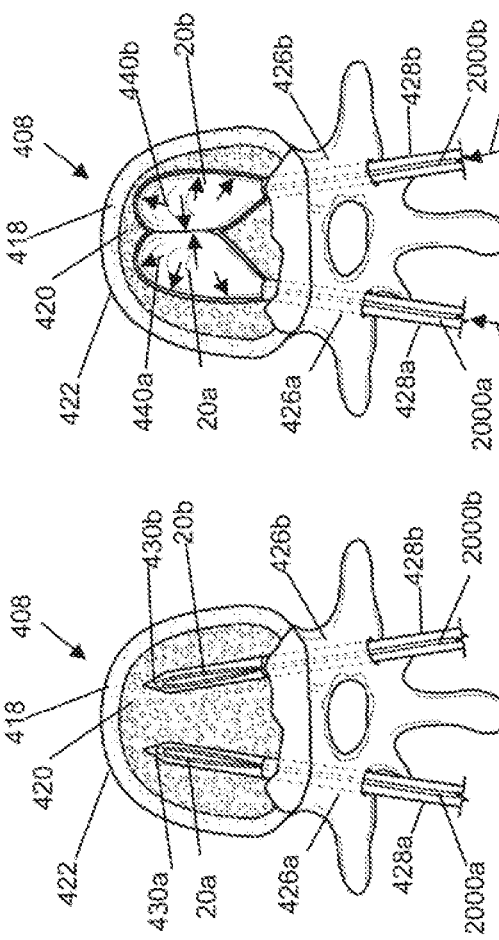
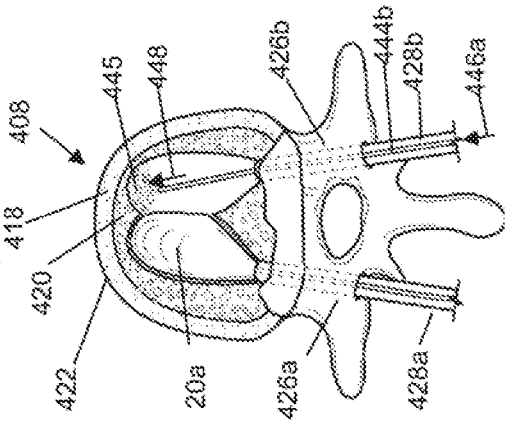
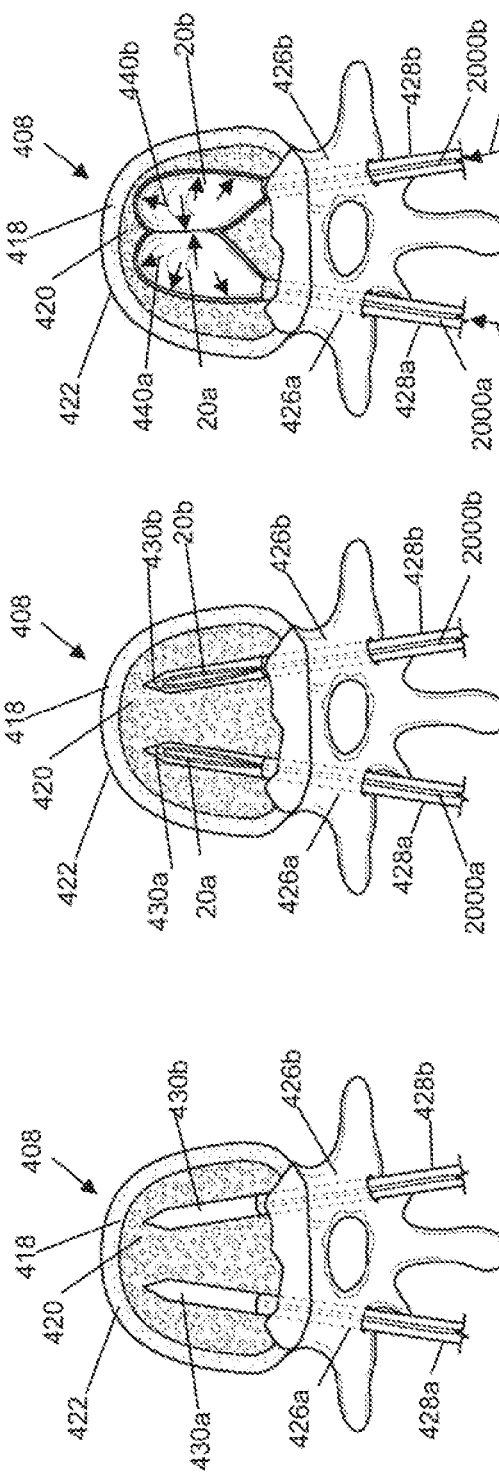
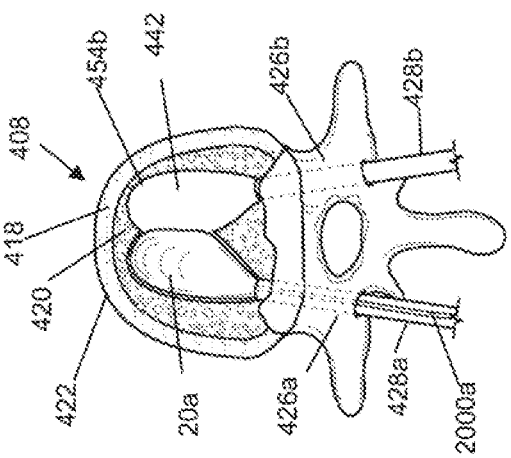

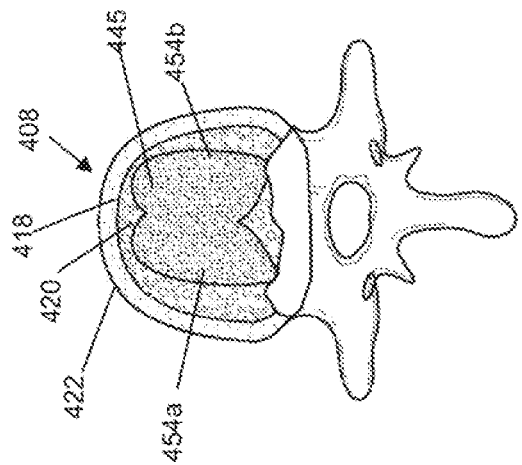
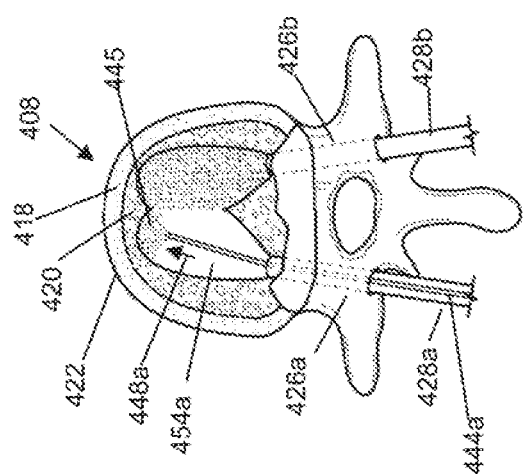
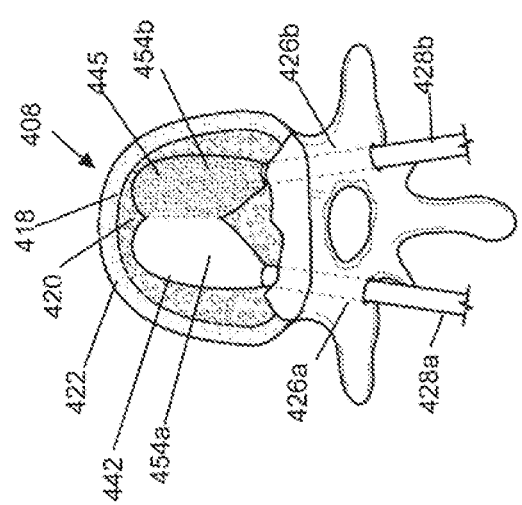

INFLATABLE MEDICAL DEVICES

CROSS-REFERENCE TO RELATED APPLICATIONS

This application claims priority to U.S. Provisional Application No. 61/411,778, filed 9 Nov. 2010, which is incorporated herein by reference in its entirety. This application is a divisional of Ser. No. 13/293,058, filed Nov. 9, 2011, which is incorporated herein by reference.

BACKGROUND

Technical Field

Devices and methods for a delivering a material into an orthopedic target site are disclosed. For example, devices and methods for delivering bone cement to a vertebral body are disclosed.

Description of Related Art

It is common during orthopedic medical procedures to place materials in the bone. For instance, in vertebroplasty, bone cement is injected to stabilize a vertebral compression fracture. Similarly, in kyphoplasty, a balloon is first inserted into a vertebral body and inflated to create a void. The void is then filled with bone cement.

Some devices for moving bone cement consist of a hand pump and a flexible tube. The tube is inserted into the orthopedic structure and bone cement is pumped through the tube and into the structure. The tube is long enough that the pump may be located up to several feet from the injection site. These devices have the advantage of allowing the physician to be removed from the injection site such that he or she is not exposed to the x-rays used to guide the filling procedure. However, tactile feedback is poor, excessive pressures can be generated and the bone cement remaining in the tube is all wasted in the end. Detaching the tube from the mass of injected bone cement can also be problematic.

Some devices, such as those used for kyphoplasty, use a simple rigid hollow tube with a solid rigid pusher rod that slides down the tube. The hollow tube is filled with bone cement and the solid pusher rod drives the bone cement into the body. These devices have the advantage of excellent tactile feedback, simplicity, lack of waste and easy termination with the mass of injected bone cement. However, they have small volumes and, because they are used right at the injection site, may expose the physician to x-rays during the filling procedure. Finally, because of their material choices, they may require significant force to extrude cement as the cement hardens.

What is needed is a device to place material into bone that protects physicians from X-ray exposure, has adequate volume, smooth operation, good haptics, minimizes waste and allows easy termination with the mass of injected bone cement.

SUMMARY OF THE INVENTION

A device for delivering a material into an orthopedic target site is disclosed. The device can have a flexible tube having a first lumen having a first end and a second end. The first lumen can extend along all or part of the length of the flexible tube. The device can have a pusher having a pusher total length. The pusher can have a pusher first length along and a pusher second length. The pusher first length can abut or contact the pusher second length. The pusher first length can have a first rigidity. The pusher second length can have a second rigidity. The first rigidity can be less than or greater than the second rigidity. The pusher and tube can be configured for the pusher to be slidably received by a port at the proximal end of the first lumen. The material to be delivered can be located in the first lumen between the pusher and the distal end of the flexible tube.

The pusher first length can be at least about 10% of the pusher total length. The pusher second length can be at least about 10% of the pusher total length.

The material can be or have a bone cement. The flexible tube can have a low friction material configured to resist binding to the bone cement.

The flexible tube can be translucent and/or transparent. The flexible tube can have a second lumen along all or part of the length of the flexible tube. The pusher second length can have a cable.

A method for delivering a material into an orthopedic target site is disclosed. The method can include slidably positioning a pusher into a first lumen of a flexible tube. The first lumen can have a first port and a second port. The pusher can have a pusher first length and a pusher second length. The pusher first length can be more rigid or less rigid than the pusher second length. The method can include loading the first lumen with the material between the pusher second length and the second port. The method can include positioning the flexible tube so the flexible tube is configured to have at least a first curve, for example to navigate around an anatomical obstruction. Positioning the flexible tube can include the second port being located at the orthopedic target site. The method can include moving the pusher from a first pusher position to a second pusher position. Moving the pusher from the first pusher position to the second pusher position can include moving the pusher second length across the first curve. The method can include deploying the material from the lumen to the orthopedic target site.

The deploying of the material is concurrent with the moving of the pusher from the first pusher position to the second pusher position. The material to be delivered to the orthopedic target site can be or have a bone cement.

The method can include stopping a flow of the material. The stopping of the flow can include ceasing a translational movement of the pusher with respect to the flexible tube.

The method can include removing the flexible tube from the orthopedic target site. The method can include creating a void at the orthopedic target site.

The method can include positioning a cannula at the orthopedic target site. The cannula can have a cannula distal port open to the orthopedic target site once the cannula is positioned. Positioning the flexible tube can include moving the flexible tube through the cannula, for example, until the distal port of the flexible tube exits the cannula distal port.

A method for delivering a material into an orthopedic target site is disclosed. The method can include positioning a device at the orthopedic target site. The pusher or advancement rod can have an advancement rod first length and an advancement rod second length. The advancement rod first length can have a different rigidity than a rigidity of the advancement rod second length. The method can include advancing the advancement rod from an advancement rod proximal position to an advancement rod distal position. During the advancing of the advancement rod, the first length of the advancement rod can be non-collinear with the advancement rod second length. The method can include deploying the material from the device to the orthopedic target site.

The material can be deployed preceding, subsequent to, concurrent with, or combinations thereof, the advancing of the advancement rod.

BRIEF DESCRIPTION OF THE DRAWINGS

FIG. 1 illustrates a variation of a void creation tool.

FIG. 2a illustrates a variation of the material delivery device.

FIG. 3 illustrates a variation of the device dissembled.

FIG. 4 illustrates a variation of the delivery device inner assembly in a curved configuration.

FIG. 5 illustrates a variation of the delivery device outer assembly in a curved configuration.

FIG. 6 is a close-up cross-section of a length of the device.

FIG. 7 is a close-up view of a length of a variation of the device.

FIG. 8 is a close-up view of a length of a variation of the proximal end of the device.

FIG. 9 is a close-up view of a length of a variation of the distal end of the device.

FIGS. 10A through 10E illustrate variations of cross-section A-A.

FIGS. 11a and 11b are close-up, phantom views of variations of the distal end of the device.

FIGS. 12a and 12b illustrate a variation of a method for controllably closing the distal end of the device.

FIGS. 13a and 13b illustrate a variation of a method for controllably closing the distal end of the device.

FIGS. 14a, 14b, 14c illustrate a variation of a method for controllably opening and closing the distal end of the device.

FIGS. 17A through 17i illustrate a method for creating one or more voids at a target site within a vertebral body, filling the voids with a filler material such as bone cement, and withdrawing surgical tools for creating the voids and delivering the filler material from the target site.

DETAILED DESCRIPTION

Figure 2B:
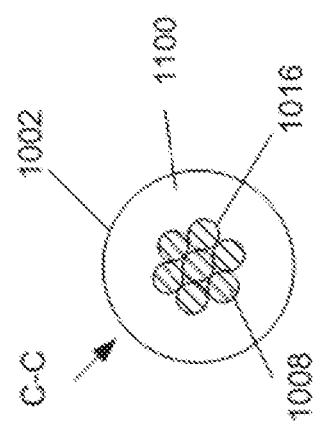
FIGS. 2b and 2c are cross-sections B-B and C-C, respectively, of a variation of the device.

FIG. 1 illustrates that an inflation system 470 can have an expandable void-creation volume such as balloon 20 that can be inflated by pushing inflation fluid, such as water, saline, a gel or dye, from the syringe 472, into the inflation port 482, through the hollow shaft lumen 154 and into the balloon 20. The syringe 472 can be detachable or non-detachable from the remainder of the inflation system 470.

The stiffening rod 474 can be removed from the inflation system 470 or left in place to stiffen the inflation system 470 while positioning the balloon 20 in the body. The stiffening rod tip 484 can have atraumatic geometry, or a soft plastic or elastomeric tip that will minimize puncture or damage the distal end of the balloon. The inflation system 470 can have a stiffening rod control 480, for example a knob or handle on the proximal end of the inflation system 470 to control the position of the stiffening rod 474. A seal 286 adjacent to the stiffening rod control can prevent pressure from escaping from the hollow shaft lumen. When the balloon 20 is at the target site, the stiffening rod 474 can be removed from the inflation system or left in place.

FIG. 2a illustrates a delivery service or system that may be used to deliver a material, such as one or more bone cements, morselized bone, or combinations thereof, into the body. Cement delivery device 996 may be comprised of cement delivery device outer assembly 1000 and cement delivery device inner assembly 1008. Inner assembly 1008 may be inserted into outer assembly 1000 such that the inner assembly 1008 can slide relative to the outer assembly 1000.

FIG. 3 shows that the cement delivery device outer assembly 1000 may comprise outer assembly tube 1002, outer assembly handle 1004, outer assembly tube end 1006 with an outer assembly tube end length 1007 and bone cement filling fitting 1032. Outer assembly tube 1002 may be comprised of a low-friction material such as PTFE, LDPE or the like. For instance, tube 1002 may be made of a material that has a dynamic coefficient of friction with steel of less than 0.3, more narrowly less than 0.2, still more narrowly less than 0.1. The low-friction material can resist binding to the bone cement.

Outer assembly tube 1002 may be flexible, rigid, semi-flexible, or combinations thereof, for example alternating along the length of the outer assembly tube 1002. Outer assembly tube 1002 may be opaque, clear, transparent, translucent or combinations thereof. Outer assembly tube 1002 may comprise a fiber reinforcement element, such as a braid. This fiber reinforcement element may increase radial stiffness when the tube 1002 is pressurized. Outer assembly tube 1002 may have an outer diameter of less than about 0.32 inches (8.1 mm), more narrowly less than 0.2 inches (5 mm). Outer assembly tube 1002 may have a length of 12-32 inches (304-813 mm). Outer assembly tube 1002 may have about a 0.138 inch (3.50 mm) outer diameter and about a 0.108 inch (2.74 mm) inner diameter and about a length of 20 inches (508 mm).

FIG. 3 shows that the cement delivery device inner assembly 1008 may comprise an inner assembly pushing device 1014 and an inner assembly handle 1012. Pusher, advancement rod, or inner assembly pushing device 1014 may comprise a pushing device rigid portion 1020 with a pushing device rigid portion length 1028, and a pushing device flexible portion 1016 with a pushing device flexible portion length 1024 and a pushing device flexible portion tip 1018.

The pushing device rigid portion length 1028 can be about 10% or more, or yet more narrowly greater than or equal to about 25%, for example about 65% of the entire length of the inner assembly pushing device 1014. The pushing device flexible portion length 1024 can be about 10% or more, or, yet more narrowly greater than or equal to about 25%, or for example about 35% of the entire length of the inner assembly pushing device 1014. The pushing device rigid portion length 1028 and the pushing device flexible portion length 1024 can combine to be about the entire length of the inner assembly pushing device 1014.

The pushing device rigid portion 1020 can abut, be integral with, or contact the pushing device flexible portion 1016. For example, the pushing device flexible portion 1016 can be a cable fused, bound, clipped, wedged into a port in the distal end of the pushing device rigid portion 1020, or combinations thereof.

The pushing device rigid portion 1020 may be a rod or a tube or a semi-rigid cable with an outside diameter of about 0.050-0.090 inches (1.27-2.29 mm). The pushing device rigid portion length 1028 may be about 7-15 inches (178-381 mm). The pushing device flexible portion 1016 may be a semi-rigid cable or semi-flexible cable with a diameter of about, 0.040-0.080 inches (1.02-2.03 mm), more narrowly 1/16 of an inch (1.59 mm). The pushing device flexible portion 1016 may be attached to the pushing device rigid portion 1020 by a bond, a crimp, a weld, a braze or some combination thereof. The pushing device flexible portion length 1024 may be about 1-7 inches (25-178 mm). The pushing device flexible portion tip 1018 may be comprised of an additional short section of tubing, a tightly bonded termination of the cable, a crimp fitting, or combinations thereof. The pushing device flexible portion 1016 may be omitted entirely from the inner assembly pushing device 1014.

Figure 2C:
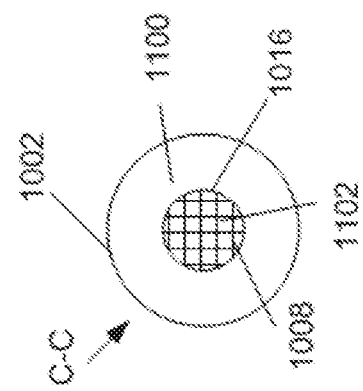

FIGS. 2b and 2c illustrate a variation of cross-sections B-B and C-C respectively. FIG. 2b illustrates that the tube 1002 can have a lumen 1100. The tube 1002 can have multiple, separated lumens. The lumen 1100 can extend all or a part of the length of the tube 1002. Along the pushing device rigid portion length 1028 the pushing device rigid portion 1020 of the inner assembly 1008 can have a uniform solid or hollow circular cross-section. FIG. 2c illustrates that along the pushing device flexible portion length 1024, the pushing device flexible portion 1016 of the inner assembly 1008 can be porous, woven and/or braided, for example, as a cable.

The diameter of the pushing device rigid portion 1020 can be greater than, equal to, or less than the diameter of the pushing device flexible portion 1016. The gap between the radially inner surface of the tube 1002 and the radially outer surface of the pushing device rigid portion 1020 and/or the pushing device flexible portion 1016 can be nominal (e.g., sufficient to allow sliding), or large enough to allow deployment delivery of bone cement or other materials through the gap.

Figure 2D:
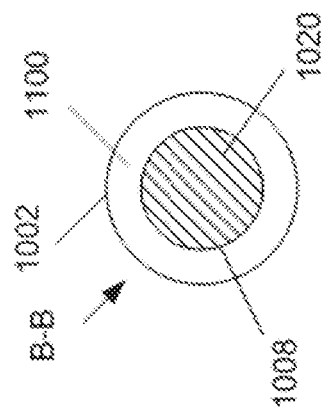
FIGS. 2d and 2e are cross-sections B-B and C-C, respectively, of a variation of the device.
Figure 2E:
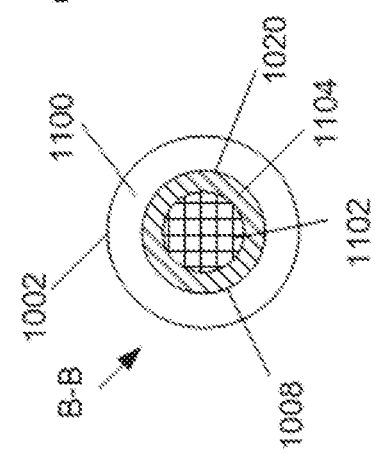

FIGS. 2d and 2e illustrate a variation of cross-sections B-B and C-C respectively. FIG. 2d illustrates that along the pushing device rigid portion length 1028 the pushing device rigid portion 1020 of the inner assembly 1008 can have a circular cross-section or cylindrical core 1102. The core 1102 can be radially surrounded by a solid or cabled stiffening sheath 1104. The core 1102 can have a smaller radius than the stiffening sheath 1104. The core can be made from the same material 1102 or a different material than the sheath 1104. FIG. 2e illustrates that along the pushing device flexible portion length 1024, the pushing device flexible portion 1016 of the inner assembly 1008 can have the core 1102, for example unsurrounded by the stiffening sheath 1104.

FIG. 4 shows that flexible portion 1016 may be bent to form an angle 1092 by applying a force 1088 normal to the longitudinal axis of flexible portion 1016 using, for instance, operator hand 1084. Angle 1092 may be greater than about 45 degrees, more narrowly greater than about 90 degrees. Force 1088 may be less than 30 newtons, more narrowly less than 15 newtons, more narrowly less than 5 newtons, still more narrowly less than 2.5 newtons For instance, pushing device flexible portion length may 1024 may be about 3 inches long, force 1088 may be about 1 newton and angle 1092 may be about 90 degrees. Applying and then removing force 1088 to flexible portion 1016 may not result in any significant permanent deformation in the shape of flexible portion 1016.

The flexible portion 1016 can be straight and/or bend having a radius of curvature of greater than or equal to about 4 in., more narrowly about 3 in, yet more narrowly about 1 in. The tube 1002, for example along the length at which the flexible portion 1016 is positioned, can curve to a radius of curvature about equal to the radius of curvature of about the radius of curvature of the flexible portion 1016, e.g., being straight, having a radius of curvature of greater than or equal to about 4 in., more narrowly about 3 in, yet more narrowly about 1 in.

FIG. 5 shows that outer assembly 1000 can be flexible. For instance, tube 1002 can be deformed into a circle without any significant permanent deformation.

FIG. 6 shows the pushing device flexible portion 1016 and the pushing device flexible portion tip 1018 sliding within outer assembly tube 1002. As shown, pushing device flexible portion 1016 and the pushing device flexible portion tip 1018 may be visible through the walls of outer assembly tube 1002.

FIG. 7 shows that outer assembly tube 1002 may be made in a curved or spiral shape. Outer assembly tube 1002 may comprise a tube reinforcement spring 1036 wrapped around the outside diameter of the tube. Spring 1036 may make tube 1002 stiffer and/or give tube 1002 a higher burst pressure.

FIG. 8 shows outer assembly handle 1004 and bone cement filling fitting 1032 attached to outer assembly tube 1002. Bone cement filling fitting 1032 may be, for instance, a luer fitting.

FIG. 9 shows a possible configuration of the outer assembly tube end 1006. Tube end 1006 may be a fitting with a smaller inside diameter than outer assembly tube 1002. Tube end 1006 can be a straight rigid tube. Outer assembly tube end 1006 may be made of a material that bonds well to bone cement. For instance, it could be made of a metal, or a porous material that bone cement may flow into.

FIGS. 10A-E show variations of cross-section A-A of outer assembly tube end 1006. Tube end 1006 can have one or more vanes 1040 that extend over all or part of the length 1007 of tube end 1006. The vanes can furcate (e.g., bifurcate, trifurcate, quadfurcate) the tube end 1006 or entire tube 1008 into multiple lumens. Vanes 1040 maybe made of a material that forms a strong bond with bone cement. Vanes 1040 may increase the area available for bone cement to bond in tube end 1006, thus increasing bond strength. Tube end 1006 may be solid except for holes 1042 that pass lengthwise through end 1006. For instance, tube end 1006 may have 1, 2, 3, 4, 5, more than 5, more than 10 or more than 50 lengthwise holes 1042. Each hole 1042 can be in fluid communication with a single lumen in the tube or each hole 1042 can be in communication with separate lumens in the tube.

FIGS. 11a and 11b show tube 1002 with tube end 1006. Tube end 1006 is, for instance, a plug which half covers the exits of tube 1002. Inner tube 1076 is sized to pass thru the inner diameter of tube 1002 and has and end plug which covers about half the exit of inner tube 1076. In one rotational orientation of inner tube 1076, shown in FIG. 11a, material may exit tube 1002 at tube end 1006. In a second rotational orientation of inner tube 1076, shown in FIG. 11b, material is blocked from exiting tube 1002. By rotating inner tube 1076 within tube end 1006, the distal end of tube 1002 may be closed. This closing may serve to sever tube end 1006 from the material immediately distal to tube end 1006.

FIGS. 12a-12b shows a material flow valve 1048. The valve 1048 may consist of a circular flapper mounted on a pivot. In FIG. 12a, the flapper is turned vertically allowing material to flow. In FIG. 12b, the flapper is turned horizontally, stopping the flow of material.

FIGS. 13a-13b show that outer assembly tube 1002 can be circumferentially closed by pulling cable 1044.

FIGS. 14a-14c show a material flow valve that is activated passively. In FIG. 14a, bone cement 445 is flowing towards cement flow valve 1048. In FIG. 14b, the bone cement 445 has reached cement flow valve 1048 and the back pressure on the bone cement 445 has caused cement flow valve 1048 to open. In FIG. 14c, the back pressure on the bone cement 445 is now not sufficient to hold cement flow valve 1048 open and it closes automatically.

Figures 15, 16:
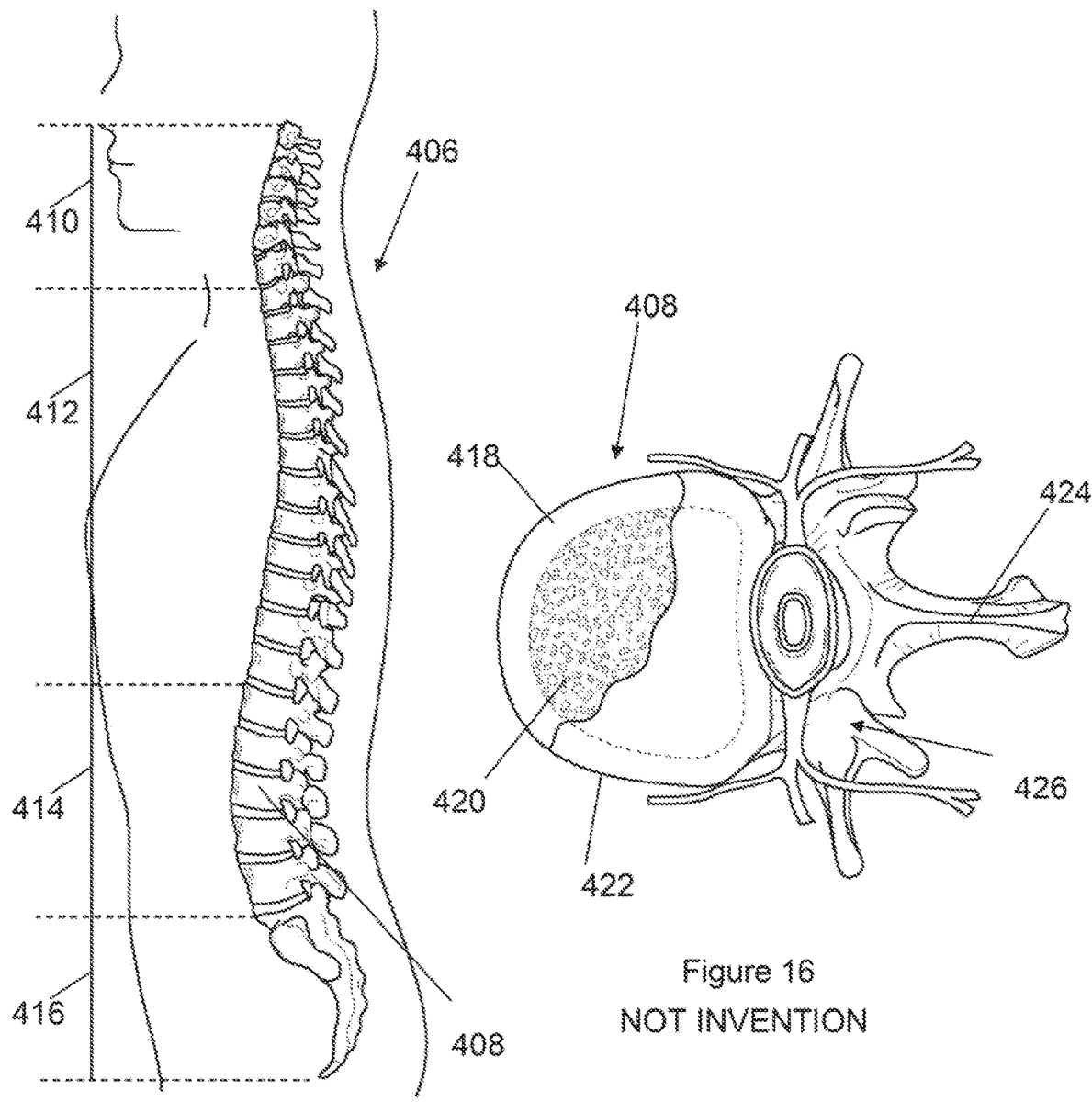
FIG. 15 is a sagittal section of a patient including a full view of a spine.
FIG. 16 is a close-up transverse section of a patient including a vertebra and the adjacent nerves including the spinal cord.

FIG. 15 illustrates a sagittal view of a patient and the spine 406. The spine 406 can have vertebrae 408 and cervical, thoracic, lumbar and sacral regions 410, 412, 414, and 416. The device 470 and 996 can be used in or between vertebrae 408 in any region of the spine 406.

FIG. 16 illustrates a vertebrae 408 that can have cortical bone 418 and cancellous bone 420. The vertebrae 408 can have a vertebral body 422 a vertebral process 424 and pedicles 426.

FIGS. 17A through 17i illustrate a method for deploying balloons 20 bilaterally, for example including one balloon inserted through each of opposing pedicles 426a and 426b.

FIG. 17A illustrates that a first delivery tube 428a, such as a cannula, can be placed through the left pedicle 426a. The delivery tube 428 may have a inside diameter of less than about 6 mm, more narrowly from about 2 mm to about 4.5 mm. A bone drill can be passed through the delivery tube to form a first drill void 430a on the left side of the vertebral body. A second delivery tube 428b can be through the right pedicle 426b. A second drill void 430b can be formed on the left side of the vertebral body.

FIG. 17B illustrates that a first balloon 20a can be inserted into the left side of the vertebral body through the first delivery tube 428a. A second balloon 20b can be inserted into the right side of the vertebral body through the second delivery tube 428b. The balloons 20a and 20b may be part of an inflation system 470, such as that shown in FIG. 1.

FIG. 17C illustrates that fluid pressure can be delivered, as shown by arrow 438, through the hollow shaft 2000 to the balloon 20. The balloon 20 can inflate and expand, as shown by arrows 440a and 440b. The expanding balloon can compress the cancellous bone surrounding the drill void, creating a larger balloon void 442. The first and second balloons can form a first void segment 454a and a second void segment 454b, respectively, of the balloon void 442. The void segments 454 may overlap, as shown. The void segments 454 may be separate.

Figure 18:
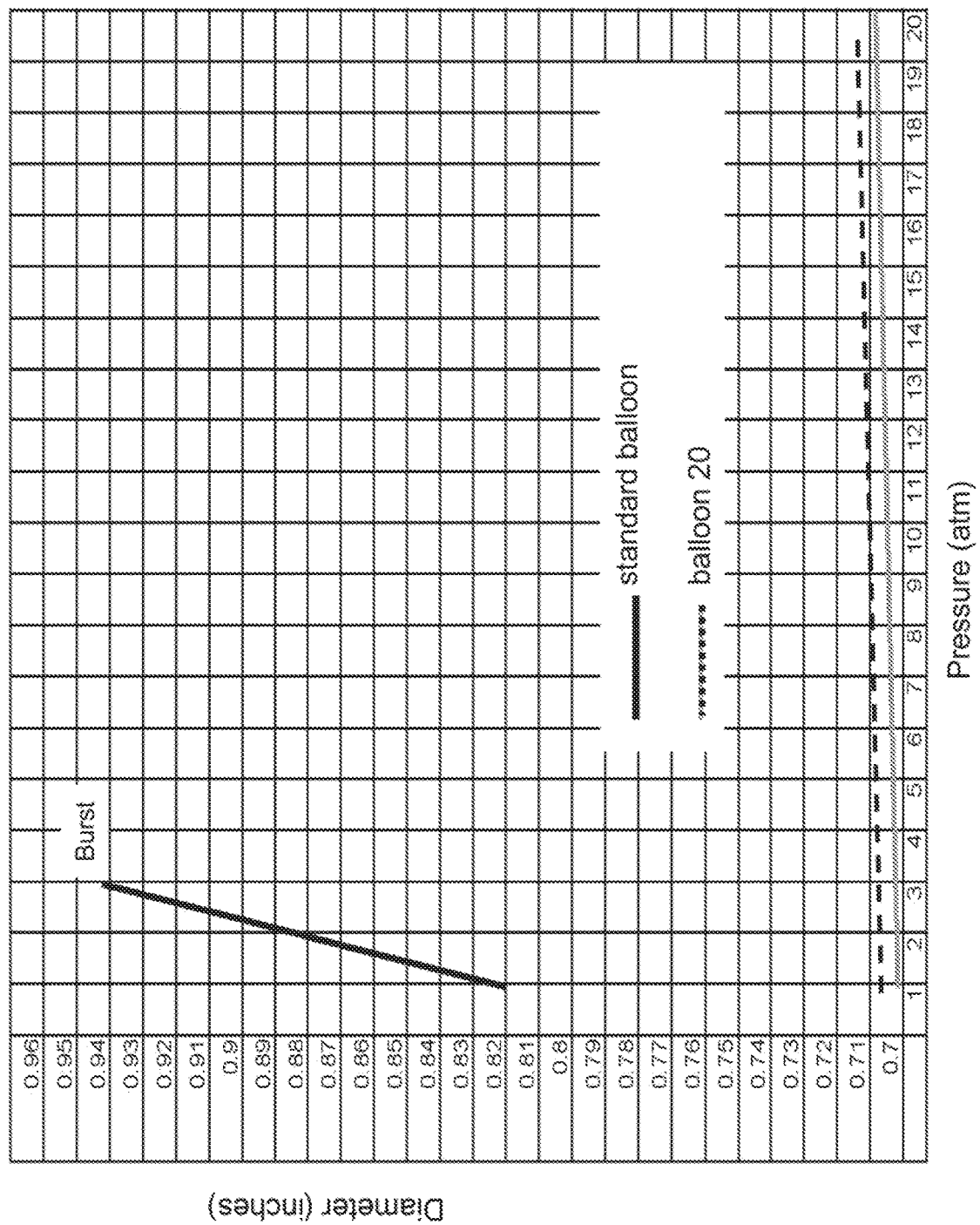
FIG. 18 is a graph showing pressure verse diameter for variations of balloons including burst pressures.

FIG. 18 illustrates that the diametric elasticity of existing medical inflatable devices can be approximately 0.06 in./ATM and that a typical burst pressure can be about 3 ATM. Balloon 20 can have an exemplary diametric elasticity of 0.0004 in./ATM and a burst pressure above 20 ATM (290 psi). For example, the burst pressure can be from about 290 psi to about 1500 psi. More narrowly, the burst pressure can be from about 500 psi to about 1000 psi. For example, the burst pressure can be about 500 psi, about 750 psi, about 1000 psi, about 1500 psi, or higher than 1500 psi. For example, the burst pressure can be greater than 4 ATM with a diameter of greater than 20 mm, with a diametric compliance of less than about 15%, or less than about 10% or less than 5%.

FIG. 17D illustrates that the second balloon 20b can be deflated, contracted and removed from the balloon void.

FIG. 17E illustrates that a second cement conduit 444b can be inserted through the second delivery tube 428b and into the second void segment 454b. Bone cement 445 can be delivered through the second cement conduit 444b and into the second void segment 454b. Cement conduits 444a and 444b may each be equivalent to outer assembly tube 1002.

FIG. 17F illustrates that the bone cement 445 can fill the second void segment 454b and/or contact the first balloon 20a. The second cement conduit 444b can be removed from the balloon void. The bone cement delivered to the second void segment can cure. The first balloon 20a may not erode, decay or bond to the cement.

FIG. 17G illustrates that the first balloon 20a can be deflated, contracted and withdrawn from the first void segment 454a.

FIG. 17H illustrates that a first cement conduit 444a can be inserted through the first delivery tube 428a and into the first void segment 454a. Bone cement 445 can be delivered through the first cement conduit 444a and into the first void segment 454a.

FIG. 17i illustrates that the first and second delivery tubes 428 can be removed from the patient. The balloon voids 454a and 454b can be substantially filled with bone cement 445. The bone cement 445 can cure.

The procedure described in FIGS. 17a to 17i and FIG. 18 may also be performed with the omission of one of the two delivery tubes 428 and wherein only a single void 454 is created with one balloon 20 using access through the remaining tube 428.

Cement delivery device outer assembly 1000 may be filled with uncured bone cement by injecting it from, for instance, a syringe attached to bone cement filling fitting 1032. Cement delivery device inner assembly 1008 may be inserted into cement device outer assembly 1000 such that advancing the inner assembly causes bone cement to be expelled at outer assembly tube end 1006. The design of outer assembly tube 1002 (such as, for instance, the choice of low friction materials) may make the movement of bone cement particularly smooth and easy, regardless of the state of cure of the bone cement. For instance, advancing inner assembly handle 1012 may require from 2-8 lbs of force. Outer assembly tube 1002 may not bond at all to bone cement as it cures. Tip 1018 may fit the inside diameter of outer assembly tube 1002 such that the tip can move freely forward without allowing any bone cement to pass around the tip 1018.

Figure 19:
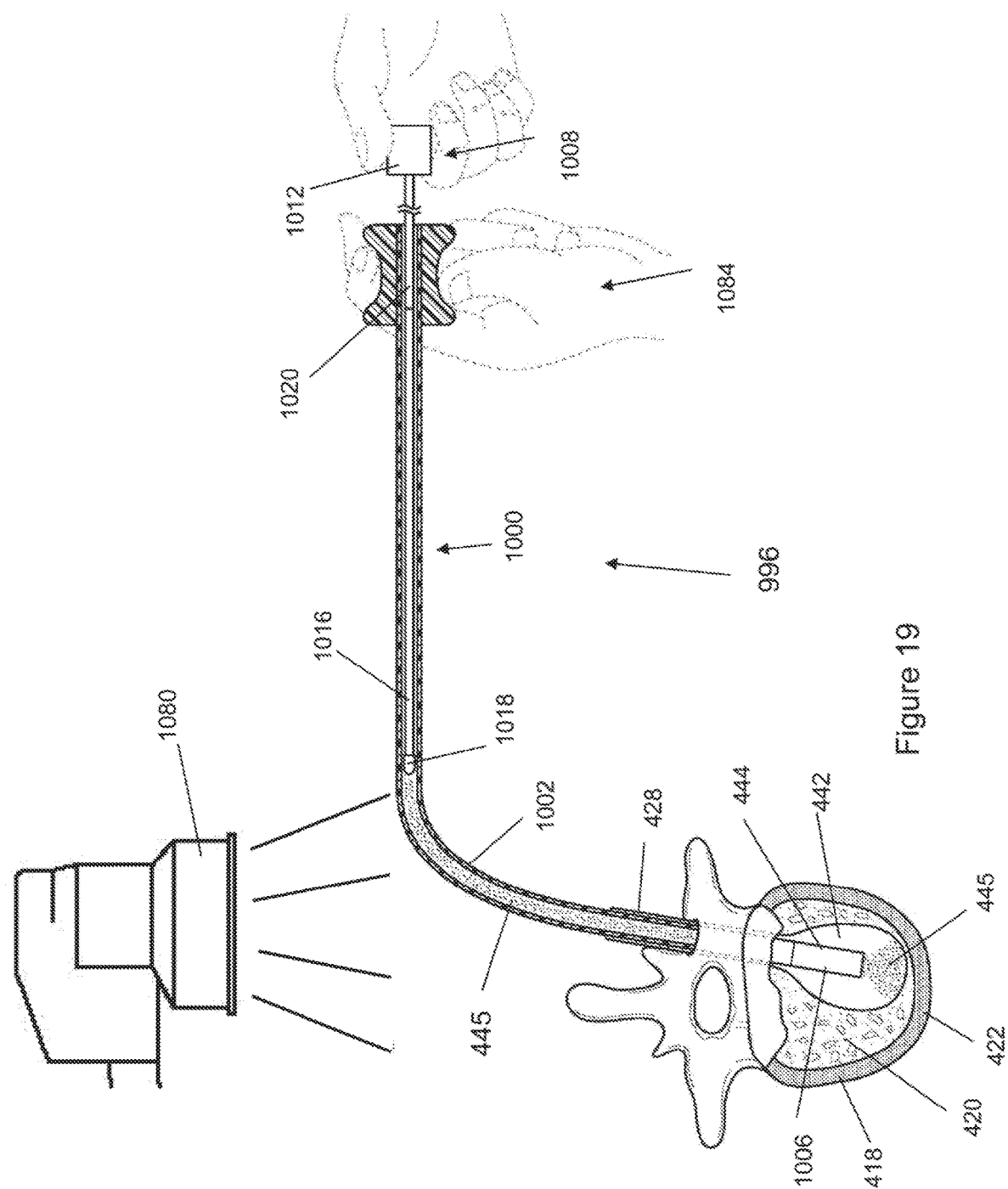
FIGS. 19 and 20 illustrate methods for using the delivery device.
Figure 20:
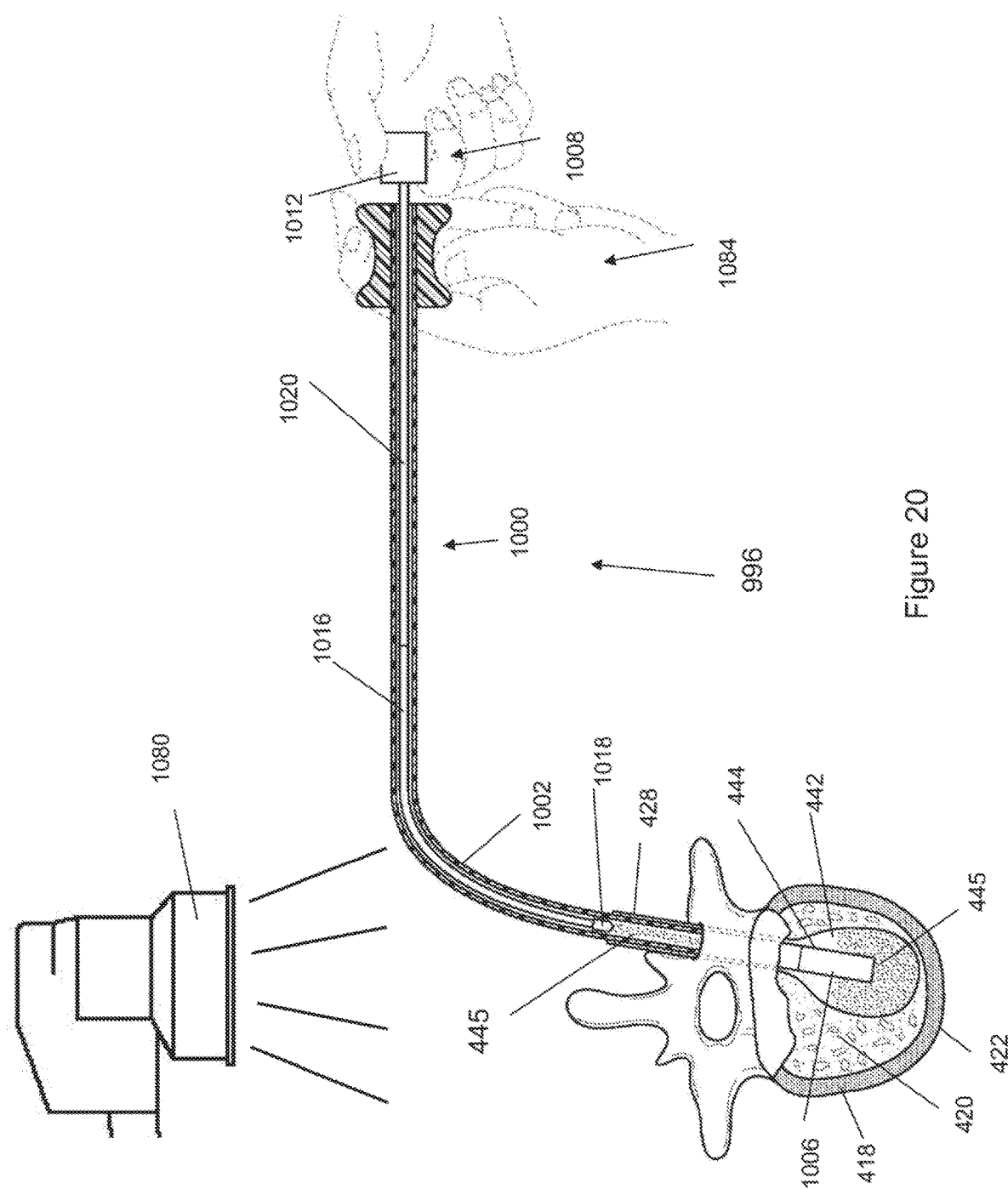

FIGS. 19 and 20 show a method for placing material in the body, for instance for placing bone cement 445 in a vertebral body 422. The bone cement 445 to be deployed from the cement delivery device 996 can be loaded into the device 996 between the distal end of the flexible portion 1016 and/or the tip 1018 and the distal port at the distal end of the device 996.

As shown in FIGS. 19 and 20, the cement delivery device 996 may be inserted through a cannula or delivery tube 428. The distal end of the device outer assembly 1000 can exit the distal end of the delivery tube 428 into the target site of the void 442. C-arm head 1080 may produce imaging x-rays for use by an operator during the procedure. Operator hands 1084 may not be in the direct x-ray path. The tube 1002 can be configured to have a curve, such as a 90° turn, while in the patient and/or outside the patient after the tube 1002 exits the patient. The tube 1002 can turn away from the C-arm head 1080, for example enabling a user (e.g., physician) to use the device to insert the bone cement 445 into the patient without exposing, or minimizing exposure of, the energy (e.g., radiation) emitted from the head 1080.

In FIG. 19, a portion of cement 445 has been placed into void 442 by translatably, slidably advancing the device inner assembly 1008 with respect to the device outer assembly 1000. Tip 1018, flexible portion 1016 and rigid portion 1020 may be visible to the operator through tube 1002. Flexible portion 1016 has no significant bend in FIG. 19.

In FIG. 20, inner assembly 1008 has been advanced distally from the position shown in FIG. 19. Flexible portion 1016 can be bent around a curve (e.g., for ergonomic improvement and/or to keep the user's hands clear of energy emitted by the C-arm head 1080, and/or to navigate around an anatomical obstacle in vivo) in tube 1002. Tip 1018 may not enter delivery tube 428. The assembly may be held as shown in FIG. 20 until the bone cement cures. Tube end 1006 may be broken free (for instance, by twisting or bending). The design of tube end 1006, such as described supra, may give a very strong bond with the cone cement in tube end 1006. This bond may make it easier to break tube end 1006 free. Cement delivery device 996 and delivery tube 428 may be removed.

The internal volume of tube 1002 may contain sufficient bone cement to fill one third of the void 442 in a vertebral body, more narrowly one half of the void 442, still more narrowly all of the cavity in a vertebral body. Inner assembly handle 1012 may give a precise haptic feedback to the user about pressure in the void 442 while bone cement 445 is being placed in the void 442.

U.S. patent application Ser. No. 12/537,166, filed 6 Aug. 2009; and Ser. No. 12/477,057, filed 2 Jun. 2009 are incorporated by reference herein in their entireties.

Any elements described herein as singular can be pluralized (i.e., anything described as "one" can be more than one), and plural elements can be used individually. Any species element of a genus element can have the characteristics or elements of any other species element of that genus. The term "comprising" is not meant to be limiting. The above-described configurations, elements or complete assemblies and methods and their elements for carrying out the invention, and variations of aspects of the invention can be combined and modified with each other in any combination.

The invention claimed is:

1. A method for delivering a material into an orthopedic target site comprising:
   slidably positioning a pusher into a first lumen of a flexible tube, wherein the first lumen has a first port and a second port, and wherein the pusher has a pusher first length and a pusher second length, and wherein the pusher first length is more rigid than the pusher second length, said pusher comprising a first member spanning the pusher first length and the pusher second length, and a stiffening sheath spanning only the pusher first length;
   loading the first lumen with the material between the pusher second length and the second port;
   positioning the flexible tube so that the flexible tube is configured having a least a first curve, and wherein positioning the flexible tube comprises the second port being located at the orthopedic target site;
   moving the pusher from a first pusher position to a second pusher position, wherein moving the pusher from the first pusher position to the second pusher position comprises moving the pusher second length across the first curve; and deploying the material from the lumen to the orthopedic target site.

2. The method of claim 1, wherein the deploying of the material is concurrent with the moving of the pusher from the first pusher position to the second pusher position.

3. The method of claim 1, wherein the material comprises a bone cement.

4. The method of claim 1, further comprising stopping a flow of the material, wherein the stopping of the flow comprises ceasing a translational movement of the pusher with respect to the flexible tube.

5. The method of claim 1, further comprising removing the flexible tube from the orthopedic target site.

6. The method of claim 1, further comprising creating a void at the orthopedic target site.

7. The method of claim 1, further comprising positioning a cannula having a cannula first end, wherein positioning the cannula comprises positioning the cannula first end at the orthopedic target site; and wherein positioning the flexible tube comprises moving the flexible tube through the cannula and that the second port exits from the first end of the cannula.

8. A method of delivering a material into an orthopedic target site comprising:
   positioning a device at the orthopedic target site, wherein the device comprises an advancement rod having an advancement rod first length and an advancement rod second length, and wherein the advancement rod first length has a different rigidity than a rigidity of the advancement rod second length, said advancement rod comprising a first member spanning the advancement rod first length and the advancement rod second length, and a stiffening sheath spanning only the advancement rod first length;
   advancing the advancement rod from an advancement rod first position to an advancement rod second position, and wherein during the advancing the advancement rod first length is non-collinear with the advancement rod second length; and
   deploying the material from the device to the orthopedic target site.

9. The method of claim 8, wherein the deploying of the material is concurrent with the advancing of the advancement rod.

10. The method of claim 8, wherein the device further comprises a flexible tube having first lumen, wherein the first lumen has a first port and a second port, and wherein positioning the device comprises positioning the second port at the orthopedic target site, and wherein deployment the material comprises deploying the material out of the second port.

11. The method of claim 10, further comprising positioning a cannula having a cannula first end, wherein positioning the cannula comprises positioning the cannula first end at the orthopedic target site; and wherein positioning the flexible tube comprises moving the flexible tube through the cannula and that the second port exits from the first end of the cannula; and the method further comprising creating a void at the orthopedic target site.

12. The method of claim 8, wherein the material comprises a bone cement.

\* \* \* \* \*